(12) United States Patent
Goto

(10) Patent No.: US 12,718,442 B2
(45) Date of Patent: Aug. 25, 2026

(54) X-RAY CT APPARATUS AND TOMOGRAPHIC IMAGE GENERATION METHOD

(71) Applicant: FUJIFILM Healthcare Corporation, Chiba (JP)

(72) Inventor: Taiga Goto, Kashiwa (JP)

(73) Assignee: FUJIFILM Corporation, Tokyo (JP)

( * ) Notice: Subject to any disclaimer, the term of this patent is extended or adjusted under 35 U.S.C. 154(b) by 210 days.

(21) Appl. No.: 18/489,855

(22) Filed: Oct. 19, 2023

(65) Prior Publication Data

US 2024/0144554 A1 May 2, 2024

(30) Foreign Application Priority Data

Oct. 26, 2022 (JP) ................................ 2022-171391

(51) Int. Cl.
*G06T 12/10* (2026.01)
*A61B 6/03* (2006.01)

(52) U.S. Cl.
CPC ............. *G06T 12/10* (2026.01); *A61B 6/032* (2013.01)

(58) Field of Classification Search
CPC ..... G06T 11/005; G06T 11/006; A61B 6/032; A61B 6/5205
See application file for complete search history.

(56) References Cited

U.S. PATENT DOCUMENTS 10,304,217 B2 5/2019 Zeng et al.
2007/0009080 A1 1/2007 Mistretta
2009/0202036 A1* 8/2009 Ziegler .................. G06T 12/20 378/19
2012/0250821 A1 10/2012 Koehler et al.
2013/0108007 A1* 5/2013 Yin ..................... A61B 6/5205 378/4

(Continued)

FOREIGN PATENT DOCUMENTS

JP 2003116841 4/2003
JP 2008520257 6/2008

(Continued)

OTHER PUBLICATIONS

"Notice of Reasons for Refusal of Japan Counterpart Application", issued on Jun. 9, 2026, with English translation thereof, p. 1-p. 7.

*Primary Examiner* — John R Wallace
(74) *Attorney, Agent, or Firm* — JCIPRNET

(57) ABSTRACT

Provided are an X-ray CT apparatus and a tomographic image generation method capable of reducing a difference in a sum of weights for each projection angle in a tomographic image.

There is provided an X-ray CT apparatus including: a projection data acquisition unit configured to acquire projection data of a subject; a reconstruction weight calculation unit configured to calculate a reconstruction weight based on the projection data; and an image generation unit configured to generate a tomographic image while weighting the projection data with the reconstruction weight, in which the reconstruction weight calculation unit is configured to calculate a reconstruction weight, which includes a reliability weight indicating a degree of reliability of the projection data, through standardization using a sum of weight coefficients obtained for each projection angle.

4 Claims, 6 Drawing Sheets

(56) References Cited

U.S. PATENT DOCUMENTS

| | | | | |
|---|---|---|---|---|
| 2014/0369463 | A1 | 12/2014 | Thibault et al. | |
| 2020/0311878 | A1* | 10/2020 | Matsuura | G06V 10/82 |

FOREIGN PATENT DOCUMENTS

| | | |
|---|---|---|
| JP | 2009500115 | 1/2009 |
| JP | 2013513452 | 4/2013 |
| JP | 2014023936 | 2/2014 |
| JP | 2020168352 | 10/2020 |

* cited by examiner

Figure 1:
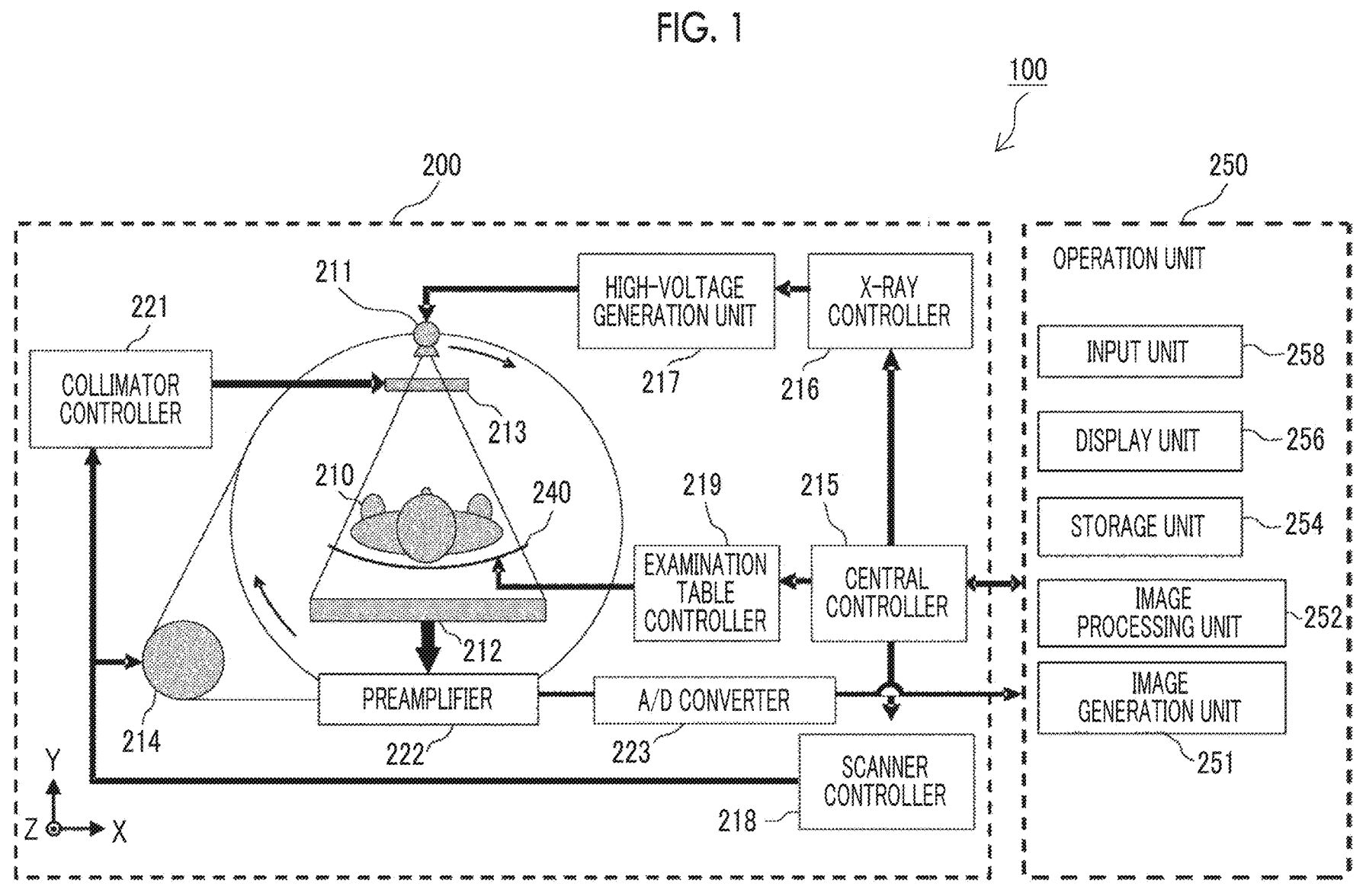

OPERATION UNIT

INPUT UNIT 258

DISPLAY UNIT 256

STORAGE UNIT 254

IMAGE PROCESSING UNIT 252

IMAGE GENERATION UNIT 251

X-RAY CONTROLLER 216

HIGH-VOLTAGE GENERATION UNIT 217

CENTRAL CONTROLLER 215

EXAMINATION TABLE CONTROLLER 219

A/D CONVERTER 223

SCANNER CONTROLLER 218

PREAMPLIFIER 222

COLLIMATOR CONTROLLER 221

211

212

213

214

210

240

X

Y

Z

X-RAY CT APPARATUS AND TOMOGRAPHIC IMAGE GENERATION METHOD

CLAIM OF PRIORITY

The present application claims priority from Japanese Patent Application JP 2022-171391 filed on Oct. 26, 2022, the content of which is hereby incorporated by reference into this application.

BACKGROUND OF THE INVENTION

1. Field of the Invention

The present invention relates to a technique for handling a tomographic image obtained by an X-ray computed tomography (CT) apparatus, and relates to a technique for improving image quality of the tomographic image.

2. Description of the Related Art

An X-ray CT apparatus is an apparatus that emits X-rays from around a subject to acquire pieces of projection data at a plurality of projection angles and that generates a tomographic image using the pieces of projection data. The generated tomographic image is used for image diagnosis as a medical image. In the tomographic image generated by back-projecting the pieces of projection data, noise increases due to noise included in some pieces of projection data.

JP2014-023936A discloses that an image is generated using a reconstruction filter that is shaped based on parameters including weight values by determining the weight value based on projection data for each view in order to reduce noise within the image without compromising computational efficiency.

SUMMARY OF THE INVENTION

However, JP2014-023936A does not take into consideration a difference in a sum of weights for each projection angle in a tomographic image. The weight value determined based on the projection data for each view reduces the difference in noise between the pieces of projection data, but may cause a difference in the sum of weights for each projection angle. The difference in the sum of the weights for each projection angle causes an artifact in the tomographic image.

In that respect, an object of the present invention is to provide an X-ray CT apparatus and a tomographic image generation method capable of reducing a difference in a sum of weights for each projection angle.

In order to achieve the above object, according to an aspect of the present invention, there is provided an X-ray CT apparatus comprising: a projection data acquisition unit configured to acquire projection data of a subject; a reconstruction weight calculation unit configured to calculate a reconstruction weight based on the projection data; and an image generation unit configured to generate a tomographic image while weighting the projection data with the reconstruction weight, in which the reconstruction weight calculation unit is configured to calculate a reconstruction weight, which includes a reliability weight indicating a degree of reliability of the projection data, through standardization using a sum of weight coefficients obtained for each projection angle.

In addition, according to another aspect of the present invention, there is provided a tomographic image generation method of generating a tomographic image using projection data of a subject, the tomographic image generation method comprising: a projection data acquisition step of acquiring the projection data; a reconstruction weight calculation step of calculating a reconstruction weight based on the projection data; and an image generation step of generating the tomographic image while weighting the projection data with the reconstruction weight, in which, in the reconstruction weight calculation step, a reconstruction weight, which includes a reliability weight indicating a degree of reliability of the projection data, is calculated through standardization using a sum of weight coefficients obtained for each projection angle.

According to the present invention, it is possible to provide an X-ray CT apparatus and a tomographic image generation method capable of reducing a difference in a sum of weights for each projection angle.

BRIEF DESCRIPTION OF THE DRAWINGS

FIG. 1 is an overall configuration diagram of an X-ray CT apparatus.

DESCRIPTION OF THE PREFERRED EMBODIMENTS

Figure 2:
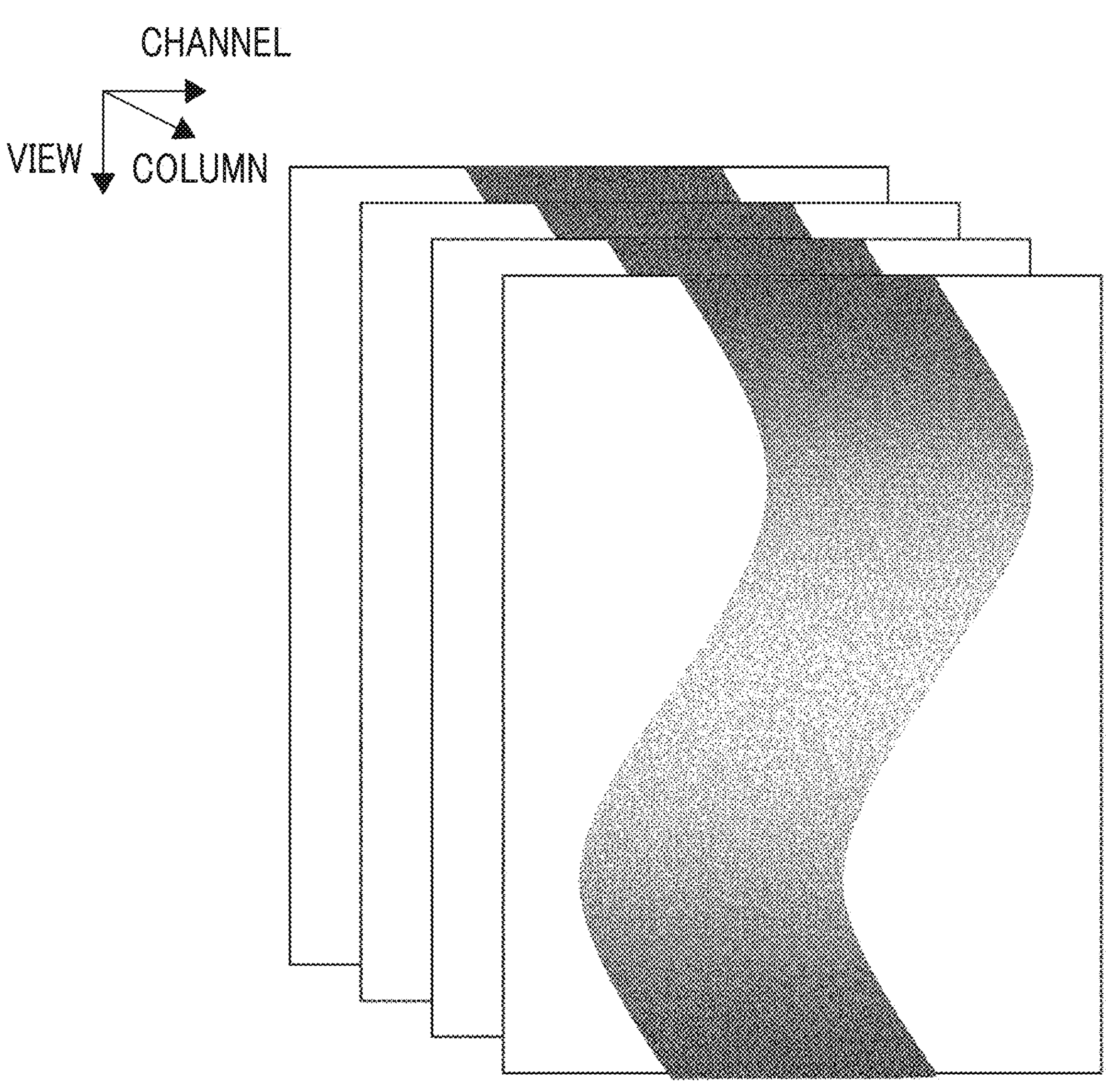
FIG. 2 is a diagram showing a configuration of projection data.

Hereinafter, examples of an X-ray CT apparatus and a tomographic image generation method according to the present invention will be described with reference to the accompanying drawings. In the following description and the accompanying drawings, components having the same functional configuration are designated by the same reference numerals, and duplicate description thereof will not be repeated.

Example 1

An overall configuration of an X-ray CT apparatus 100 will be described with reference to FIG. 1. In FIG. 1, a horizontal direction is denoted by an X axis, a vertical direction is denoted by a Y axis, and a direction perpendicular to a paper surface is denoted by a Z axis. The X-ray CT apparatus 100 comprises a scanner 200 and an operation unit 250. The scanner 200 includes an X-ray tube 211, a detector 212, a collimator 213, a drive unit 214, a central controller 215, an X-ray controller 216, a high-voltage generation unit 217, a scanner controller 218, an examination table controller 219, a collimator controller 221, a preamplifier 222, an A/D converter 223, an examination table 240, and the like.

The X-ray tube 211 is a device that irradiates a subject 210 mounted on the examination table 240 with X-rays. A high voltage generated by the high-voltage generation unit 217 is applied to the X-ray tube 211 in accordance with a control signal transmitted from the X-ray controller 216, whereby the subject is irradiated with X-rays from the X-ray tube 211.

The collimator 213 is a device that limits an irradiation range of X-rays emitted from the X-ray tube 211. The irradiation range of X-rays is set in accordance with a control signal transmitted from the collimator controller 221.

The detector 212 is a device that measures a spatial distribution of transmitted X-rays by detecting X-rays transmitted through the subject 210. The detector 212 is disposed to face the X-ray tube 211, and a large number of detection elements are two-dimensionally arranged within a plane facing the X-ray tube 211. A signal measured by the detector 212 is amplified by the preamplifier 222 and then converted into a digital signal by the A/D converter 223. After that, various kinds of correction processing are performed on the digital signal, and projection data is acquired.

The drive unit 214 rotates the X-ray tube 211 and the detector 212 around the subject 210 in accordance with a control signal transmitted from the scanner controller 218. The X-ray irradiation and the detection are performed with the rotation of the X-ray tube 211 and of the detector 212, whereby pieces of projection data are acquired from a plurality of projection angles. A data collection unit for each projection angle is called a view. In the arrangements of the two-dimensionally arranged detection elements of the detector 212, a rotation direction of the detector 212 is called a channel, and a direction orthogonal to the channel is called a column. As shown as an example in FIG. 2, the projection data is identified by the view, the channel, and the column.

The examination table controller 219 controls the operation of the examination table 240 to keep the examination table 240 stationary or move the examination table 240 at a constant speed in a Z-axis direction, which is a body axis direction of the subject 210, while the X-ray irradiation and the detection is performed. A scan performed in a state in which the examination table 240 is kept stationary is called an axial scan, and a scan performed while the examination table 240 is moved is called a spiral scan.

The central controller 215 is a device that controls the operation of the scanner 200 described above in accordance with an instruction from the operation unit 250, and specifically, is a central processing unit (CPU), a micro processor unit (MPU), or the like.

The operation unit 250 will be described. The operation unit 250 includes an image generation unit 251, an image processing unit 252, a storage unit 254, a display unit 256, an input unit 258, and the like.

The image generation unit 251 is a device that generates a tomographic image using the projection data acquired by the scanner 200, and specifically, is a CPU, a graphical processing unit (GPU), or the like. The image processing unit 252 is a device that performs various kinds of image processing in order to make a tomographic image suitable for diagnosis, and specifically, is a CPU, a GPU, or the like.

The storage unit 254 is a device that stores the projection data, the tomographic image, or an image after image processing, and specifically, is a hard disk drive (HDD), a solid state drive (SSD), or the like. The display unit 256 is a device that displays the tomographic image or the image after image processing, and specifically, is a liquid crystal display or the like. The input unit 258 is a device that is used when an operator sets acquisition conditions (a tube voltage, a tube current, a scan speed, and the like) for the projection data and reconstruction conditions (a reconstruction filter, an FOV size, and the like) for the tomographic image, and specifically, is a keyboard, a mouse, a touch panel, and the like. The mouse may be another pointing device such as a track pad or a track ball.

Figure 3:
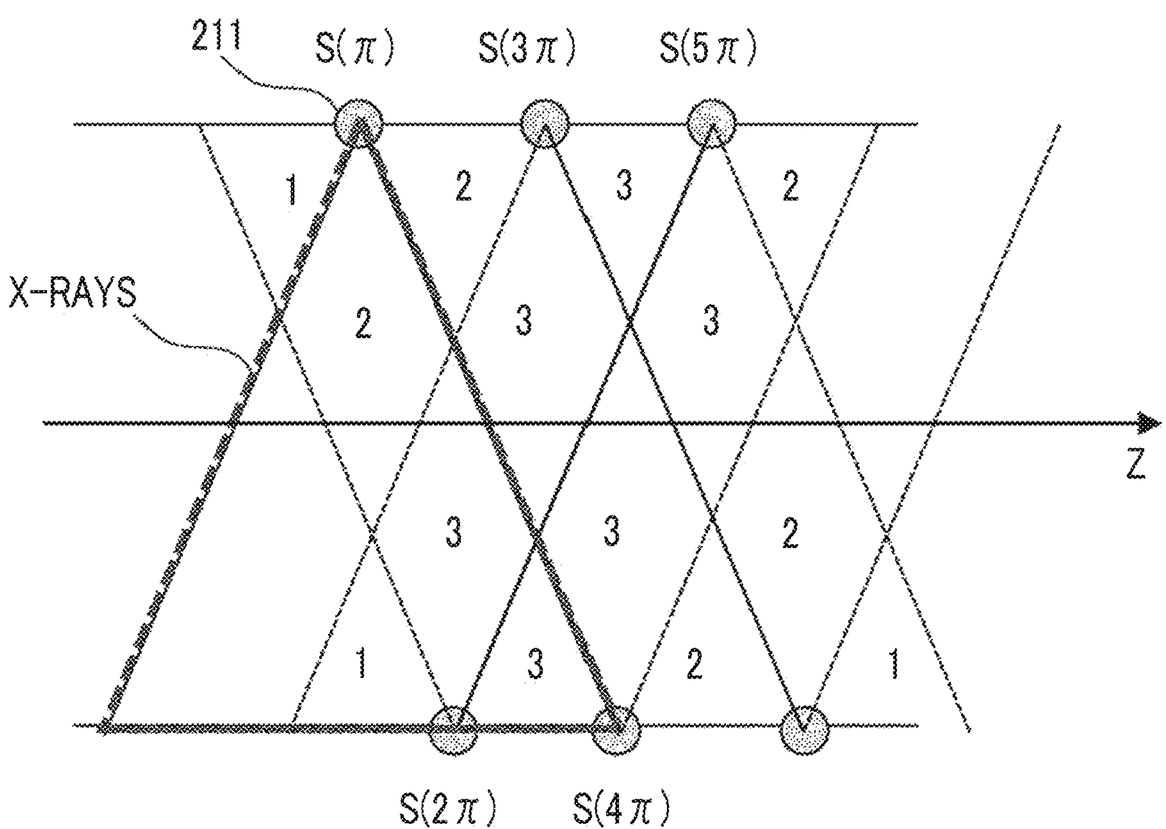
FIG. 3 is a diagram showing a difference in the number of measurements for each imaging region.

A difference in the number of measurements for each imaging region will be described with reference to FIG. 3. FIG. 3 shows the number of measurements for each imaging region during the spiral scan. Since the projection data is obtained by measuring the imaging region, the number of available pieces of projection data varies for each projection angle. That is, in a case where a weight coefficient is determined for each piece of projection data, a difference in the sum of weights for each projection angle occurs due to a difference in the number of measurements, which may cause an artifact in the tomographic image. In that respect, in Example 1, the reconstruction weight with which the projection data is weighted is calculated through standardization using the sum of the weight coefficients obtained for each projection angle. By using the standardized reconstruction weights, the difference in the sum of the weights for each projection angle is reduced, and the artifact in the tomographic image is reduced.

An example of a flow of processing executed in Example 1 will be described step by step with reference to FIG. 4.

S401

The image generation unit 251 acquires the projection data. The projection data may be calculated based on the detector output output by the detector 212 or may be read out from the storage unit 254.

S402

The image generation unit 251 calculates various weight coefficients based on the projection data acquired in S401. The weight coefficient includes, for example, a reliability weight, a channel weight, a column weight, and a view weight. Hereinafter, each weight coefficient will be described.

Reliability Weight

The reliability weight is a weight coefficient that indicates a degree of reliability of the projection data and that is larger than zero, and is set, for example, based on the magnitude of the detector output, the distance from the center of pixels of the tomographic image, or the quality of the detection element with which the projection data is measured. For the calculation of a reliability weight w_rel, for example, Equation 1 is used.

$$w\_rel = w\_out \times w\_dist \times w\_qual \quad \text{(Equation 1)}$$

Here, w_out represents a weight coefficient related to the detector output, w_dist represents a weight coefficient related to the distance from the center of the pixels, and w_qual represents a weight coefficient related to the quality of the detection element, and these weight coefficients are each set to a value larger than zero.

Figure 5:
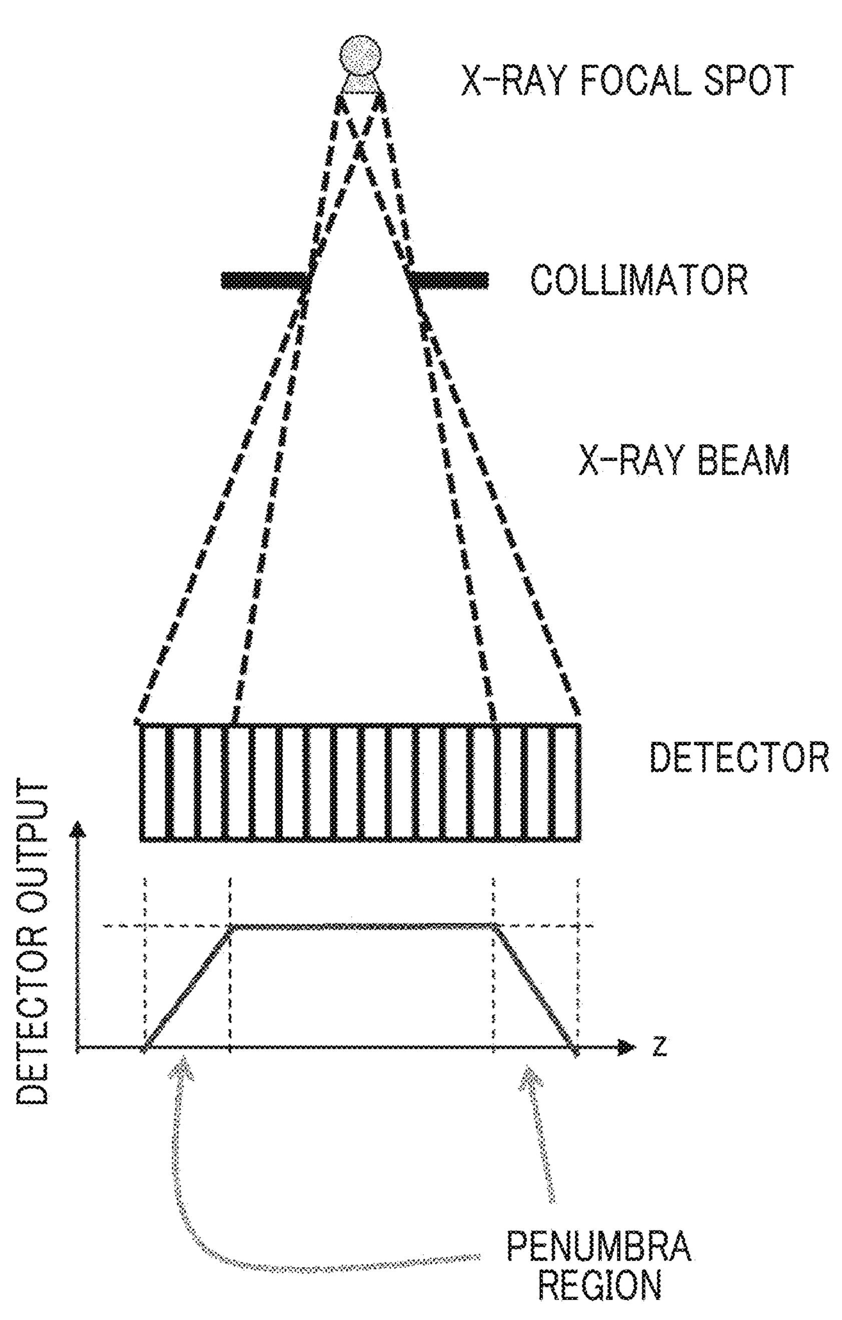
FIG. 5 is a diagram illustrating a detector output in a penumbra region.

The weight coefficient w_out related to the detector output is set to a larger value for projection data having a higher detector output. For example, in a case where the detector output is denoted by d, the statistical noise amount included in the detector output is represented by $\sqrt{d}$, and the signal-to-noise ratio is proportional to $\sqrt{d}$ ($=d/\sqrt{d}$), so that the square root of the detector output is used as the weight coefficient. In addition, since, due to a finite size of an X-ray focal spot, a penumbra region, which is generated at an end part of the detector in a column direction as shown as an example in FIG. 5, has a low detector output and a low signal-to-noise ratio, the square root of the detector output may also be used as the weight coefficient in the penumbra region.

In addition, the weight coefficient w_dist related to the distance from the center of the pixels is set to a larger value for projection data that is closer to the center of the pixels. For example, in a case of obtaining a pixel value in the tomographic image through back-projection, projection data passing through the center of the pixels is calculated through high-order interpolation processing using the projection data obtained by the measurement. The projection data calculated through the interpolation processing has a smaller error and a higher degree of reliability as the distance from the projection data obtained by the measurement is closer. Therefore, a larger weight coefficient is set for projection data that is closer to the center of the pixels.

In addition, the weight coefficient w_qual related to the quality of the detection element is set to a smaller value for projection data measured with a detection element that has inferior sensitivity and non-linearity. For example, a smaller weight coefficient is set for projection data measured with a detection element that has higher sensitivity variations or non-linearity. The projection data measured with the detection element that has inferior sensitivity and non-linearity may be replaced with an estimated value calculated using surrounding projection data.

Channel Weight

A channel weight w_ch is a weight coefficient set based on a channel position of the detector 212. In a case where the subject is not protruding beyond the detector 212, all the channel weights have the same value. In addition, since projection data is missing outside the detector 212 in a case where the subject is protruding beyond the detector 212, an estimated value is assigned to the missing projection data, and the channel weight is set based on the reliability of the estimated value. The estimated value is obtained based on the projection data of the end part channel, and the channel width of the projection data to which the estimated value is assigned is approximately 5% to 10% of an actual channel width.

Column Weight

A column weight w_raw is a weight coefficient that is set based on the column position of the detector 212, and a small weight coefficient is set at the end part in the column direction. The column width for which a small column weight is set is approximately 5% to 10% of an actual column width.

View Weight

A view weight w_view is a weight coefficient that is set based on a position in a view direction, and a small weight coefficient is set at an end part in the view direction. The view width for which a small view weight is set is approximately equal to the reciprocal of the beam pitch or slightly wider than that in terms of the number of rotations.

In a case where a value close to zero is set for the reliability weight, the channel weight, the column weight, or the view weight, it is desirable to continuously change the adjacent weight coefficients.

S403

The image generation unit 251 calculates the reconstruction weight based on the various weight coefficients calculated in S402. The reconstruction weight is calculated through standardization using the sum of the weight coefficients obtained for each projection angle. For the calculation of a reconstruction weight R, for example, Equation 2 is used.

$$R=w\_p/\Sigma w\_p \quad \text{(Equation 2)}$$

Here, w_p represents the weight coefficient of the projection data, and Σw_p represents the sum of the weight coefficients of pieces of projection data at the same projection angle. For the calculation of the weight coefficient w_p of the projection data, for example, Equation 3 is used.

$$w\_p=w\_\mathrm{rel}\times w\_ch\times w\_\mathrm{raw}\times w\_\mathrm{view} \quad \text{(Equation 3)}$$

Here, w_rel represents the reliability weight, w_ch represents the channel weight, w_raw represents the column weight, and w_view represents the view weight.

Figure 6:
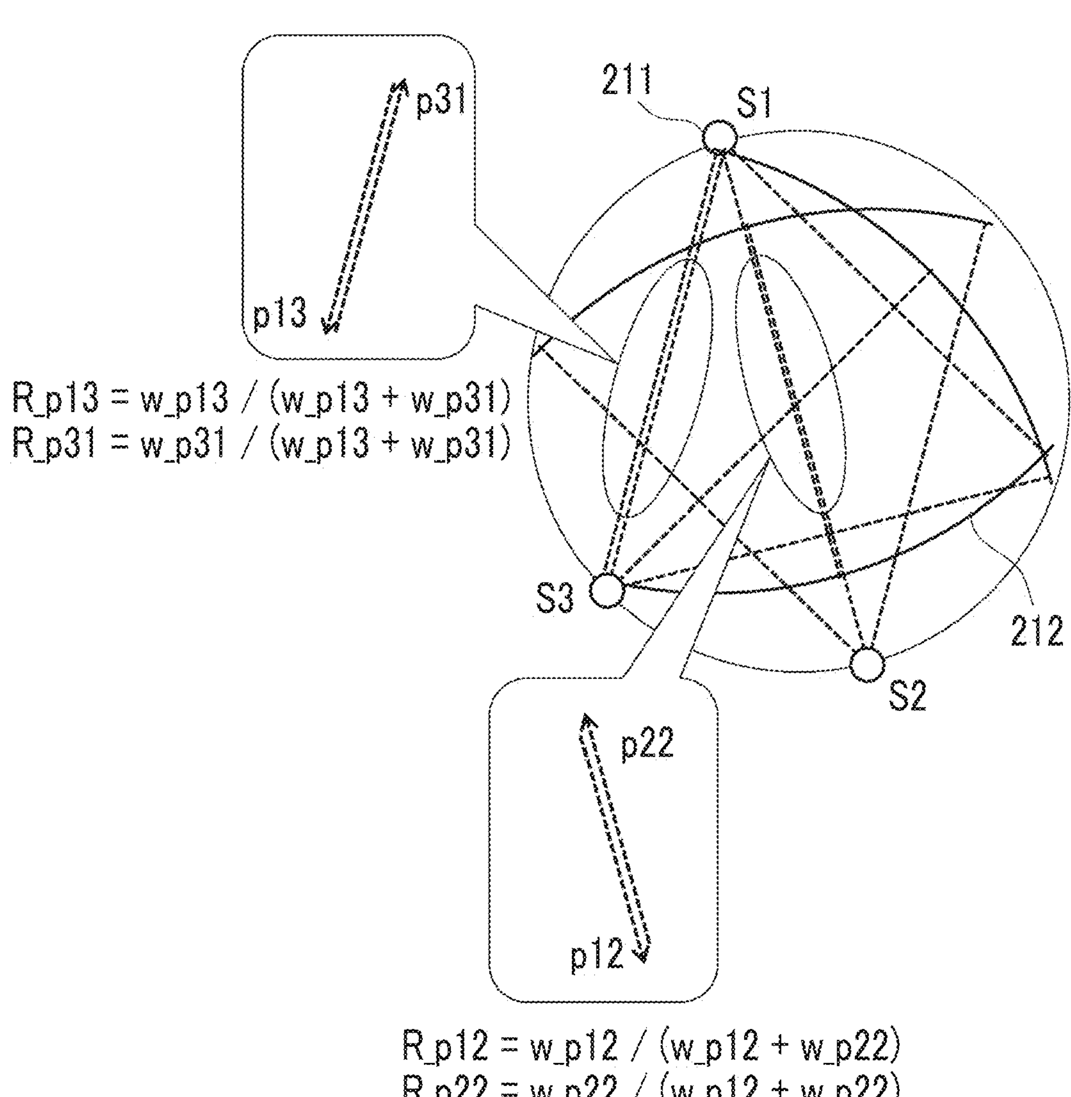
FIG. 6 is a diagram illustrating calculation of a reconstruction weight through standardization of a weight for each projection angle.

A specific example of (Equation 2) will be described with reference to FIG. 6. FIG. 6 shows pieces of projection data measured in a case where the X-ray tube 211 is located at positions S1, S2, and S3. In order to simplify the illustration, the pieces of projection data measured at the position S1 are denoted by p11, p12, and p13, the pieces of projection data at the position S2 are denoted by p21, p22, and p23, and the pieces of projection data at the position S3 are denoted by p31, p32, and p33. Further, the weight coefficient of p11 is denoted by well, and the reconstruction weight of p11 is denoted by R_p11. Similar denotations are used for the weight coefficients and reconstruction weights of other pieces of projection data.

Since the pieces of projection data p13 and p31 have the same projection angle, the sum of the weight coefficients of the projection data having the same projection angle as the projection data p13 is (w_p13+w_p31). The reconstruction weight R_p13 is calculated by standardizing the weight coefficient w_p13 of p13 with the sum of the weight coefficients (w_p13+w_p31), so that reconstruction weight R_p13 is represented by Equation 4.

$$R\_p13=w\_p13/(w\_p13+w\_p31) \quad \text{(Equation 4)}$$

Similarly, the reconstruction weight R_p31 is represented by Equation 5.

$$Rp\_31=w\_p31/(w\_p13+w\_p31) \quad \text{(Equation 5)}$$

Further, since the pieces of projection data p12 and p22 have the same projection angle, the reconstruction weights Rp_12 and Rp_22 are represented by Equations 6 and 7, respectively.

$$Rp\_12=w\_p12/(w\_p12+w\_p22) \quad \text{(Equation 6)}$$

$$Rp\_22=w\_p22/(w\_p12+w\_p22) \quad \text{(Equation 7)}$$

S404

The image generation unit 251 generates the tomographic image based on the projection data acquired in S401 and the reconstruction weight calculated in S403. More specifically, the tomographic image is generated by back-projecting the projection data weighted with the reconstruction weight.

Figure 4:
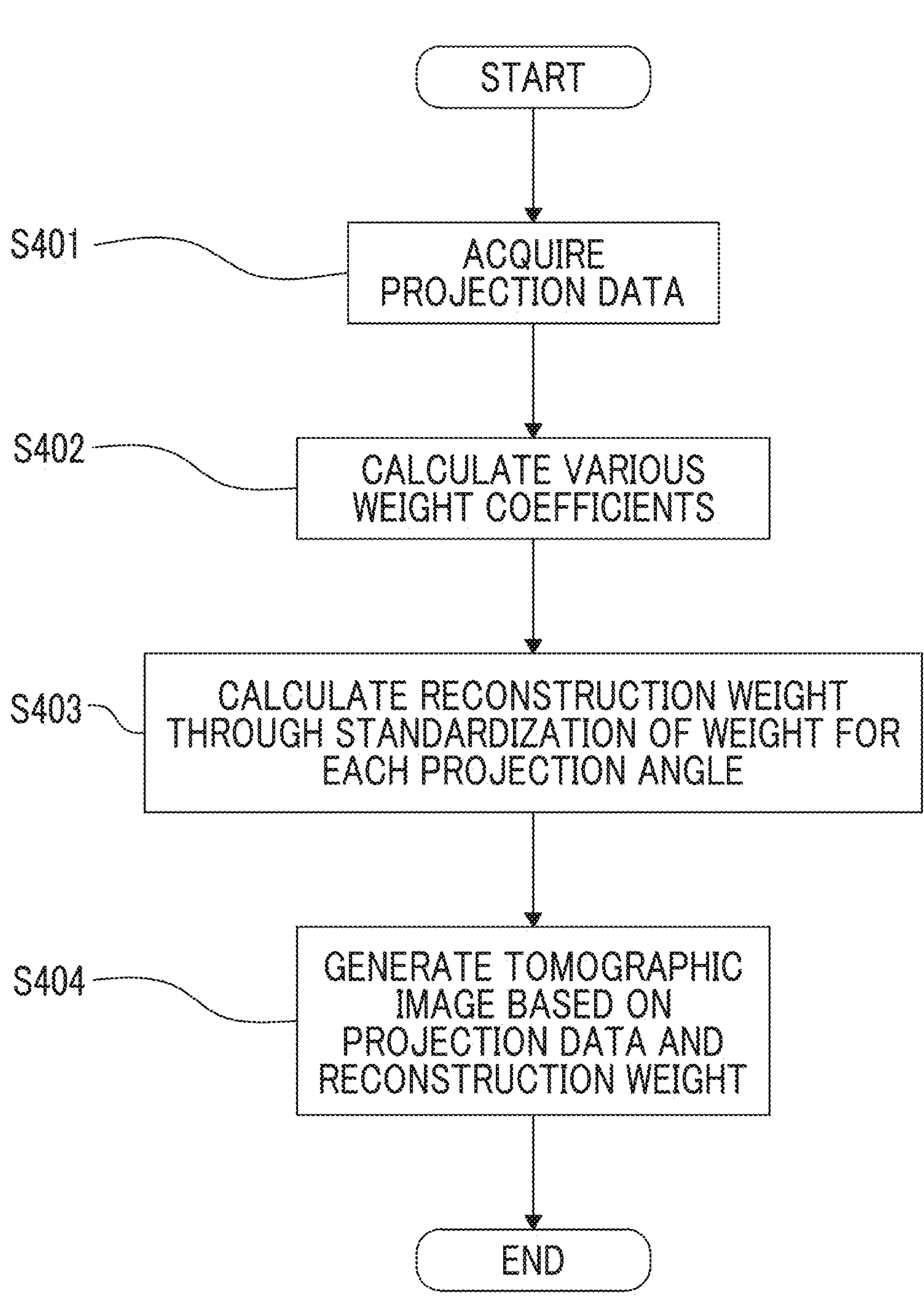
FIG. 4 is a diagram showing an example of a flow of processing of Example 1.

By the flow of the processing shown as an example in FIG. 4, the standardized reconstruction weight is calculated for each projection angle, and the calculated reconstruction weight is used to generate the tomographic image, so that the difference in the sum of the weights for each projection angle is reduced. As a result, the artifact of the tomographic image can be reduced.

Examples of the present invention have been described above. It should be noted that the present invention is not limited to the above-described examples, and the components can be modified and embodied without departing from the gist of the invention. In addition, a plurality of components disclosed in the above-described examples may be combined as appropriate. Further, some components may be deleted from all the components described in the above-described examples.

EXPLANATION OF REFERENCES

100: X-ray CT apparatus
200: scanner
210: subject
211: X-ray tube
212: detector
213: collimator
214: drive unit
215: central controller
216: X-ray controller
217: high-voltage generation unit
218: scanner controller
219: examination table controller
221: collimator controller
222: preamplifier
223: A/D converter
240: examination table
250: operation unit
251: image generation unit
252: image processing unit
254: storage unit
256: display unit
258: input unit

What is claimed is:

1. An X-ray CT apparatus comprising:
a scanner configured to acquire projection data of a subject and comprises a radiation tube; and
a processor configured to:
calculate a plurality of reconstruction weight coefficients based on the projection data;
calculate a reconstruction weight based a weight coefficient of the projection data divided by a sum of the plurality of reconstruction weight coefficients of pieces of the projection data at a same projection angle; and
generate a tomographic image based on the projection data and the reconstruction weight, wherein:
the plurality of reconstruction weight coefficients comprises a reliability weight coefficient which increases for projection data having a higher detector output, and
the reliability weight coefficient increases for projection data that is closer to a center of pixels in the tomographic image.

2. An X-ray CT apparatus comprising:
a scanner configured to acquire projection data of a subject and comprises a radiation tube; and
a processor configured to:
calculate a plurality of reconstruction weight coefficients based on the projection data;
calculate a reconstruction weight based a weight coefficient of the projection data divided by a sum of the plurality of reconstruction weight coefficients of pieces of the projection data at a same projection angle; and
generate a tomographic image based on the projection data and the reconstruction weight, wherein:
the plurality of reconstruction weight coefficients comprises a reliability weight coefficient which increases for projection data having a higher detector output, and
the reliability weight coefficient decreases for projection data measured with a detection element that has inferior sensitivity and non-linearity.

3. The X-ray CT apparatus according to claim 2,
wherein the projection data obtained from the detection element that has inferior sensitivity and non-linearity is replaced with an estimated value calculated using surrounding projection data.

4. A tomographic image generation method of generating a tomographic image using projection data of a subject, the tomographic image generation method comprising:
acquiring the projection data;
calculating a plurality of reconstruction weight coefficients based on the projection data;
calculating a reconstruction weight based a weight coefficient of the projection data divided by a sum of the plurality of reconstruction weight coefficients of pieces of the projection data at a same projection angle; and
generating the tomographic image based on the projection data and the reconstruction weight, wherein:
the plurality of reconstruction weight coefficients comprises a reliability weight coefficient which increases for projection data having a higher detector output, and
the reliability weight coefficient increases for projection data that is closer to a center of pixels in the tomographic image.

* * * * *